United States Patent [19]

Ashmead

[11] 4,169,717

[45] Oct. 2, 1979

[54] SYNERGISTIC PLANT REGULATORY COMPOSITIONS

[76] Inventor: Harvey H. Ashmead, P.O. Box 750, Clearfield, Utah 84015

[21] Appl. No.: 843,970

[22] Filed: Oct. 20, 1977

[51] Int. Cl.² .................... A01N 9/12; A01N 9/00; A01N 9/22; A01N 9/24

[52] U.S. Cl. .................................... 71/89; 71/77; 71/92; 71/96; 71/97; 71/114; 71/117; 71/118; 71/120; 71/127; 71/79

[58] Field of Search ............... 71/77, 79, 97, 89, 120, 71/92, 117, 96, 118

[56] References Cited

U.S. PATENT DOCUMENTS

| | | | |
|---|---|---|---|
| 2,806,306 | 8/1957 | Leopold et al. | 71/77 |
| 2,903,455 | 9/1959 | Strong et al. | 71/77 |
| 3,118,753 | 1/1964 | Shive et al. | 71/77 |
| 3,738,822 | 6/1973 | Asahi et al. | 71/89 |
| 3,873,296 | 3/1975 | Ashmead et al. | 71/77 |

FOREIGN PATENT DOCUMENTS

| | | | |
|---|---|---|---|
| 1270879 | 10/1960 | France | 71/77 |
| 46254 | 6/1971 | Japan | 71/79 |
| 513651 | 5/1976 | Japan | 71/89 |
| 7505401 | 11/1975 | Netherlands | 71/89 |

*Primary Examiner*—Glennon H. Hollrah
*Attorney, Agent, or Firm*—Criddle, Thorpe & Western

[57] ABSTRACT

A combination of (1) metal proteinates consisting of chelation products of an essential bivalent metal with at least two ligands which are protein hydrolysates consisting of polypeptides, peptides and naturally occurring amino acids and (2) a plant growth hormone consisting of auxins, cytokinins and gibberellin(s) singularly or in combination.

11 Claims, No Drawings

SYNERGISTIC PLANT REGULATORY COMPOSITIONS

BACKGROUND OF THE INVENTION

It is known that metal proteinates are absorbed by plants and affect the growth thereof. U.S. Pat. No. 3,873,296 aptly illustrates this phenomenon. However plants need more than just minerals and nutrients such as N-P-K mixes to affect plant growth. It is known that plants produce hormones such as cytokinins, auxins, and gibberellin(s) which also affect plant growth. Inorganic mineral salts are not absorbed intact and translocated as such throughout plants. Thus, they do not provide the minerals to the plant cells as rapidly as metal proteinates. Inorganic mineral salts are not synergistic with plant hormones and their use with plant hormones range from little to no value when compared to the present invention. Before mineral salts can be of value, the plant must alter its composition whereas metal proteinates are absorbed intact and translocated throughout the plant as metal proteinates.

Metal proteinates are actually chelates formed from a soluble bivalent metal salt and two or more protein hydrolysate ligands. By bivalent metal salt is meant a metal having an oxidation state of at least two or higher. For example transition metals may assume more than one oxidation state. In addition many metal salts carry from two to eight, and sometimes more, waters of hydration which are referred to as coordination numbers of the metal. The coordination number and valence may be different; however, the waters of hydration are attached to the metal by coordination bonding with the oxygen atom of the water supplying the necessary electrons. For example a ferrous sulfate salt may exist as such:

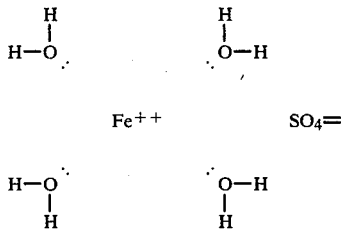

When a chelate is formed the anion is replaced and the metal ion is neutralized so that the corresponding chelate has no net electrical charge. In this manner the metal is transported through the plant more easily.

In order for the plants to have the metal ion in the right place at the right time it is important that the stability constant of the metal chelate be just right. Ligands such as citrates and ascorbates are weak complexes and perhaps even chelates but are easily broken down into their component parts. On the other hand, EDTA (ethylenediaminetetraacetic acid) and its salts form such strong chelates that they pass through an organism largely unaffected. The hydrolysis products of proteins seem to form just the right chelates and are referred to as metal proteinates. A chelate or proteinate is a heterocyclic structure which involves, in this case, at least two ligands. A ligand is the protein hydrolysate used to combine with the metal to form the proteinate and consists of a polypeptide, peptide, or naturally occurring amino acid.

Utilizing glycine, the simplist amino acid, a metal proteinate may thus be formed as follows:

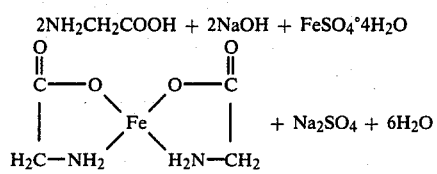

However the reaction is not quite that simple. It is important that all excess protons be removed from the protein hydrolysate prior to its reaction with the metal salt. In other words the protein hydrolysate should be on the basic side of its zwitterion state and thus possesses an excess of electrons where the protons have been removed. Glycine then might be represented as:

in its zwitterion state. The glycine, or other ligand is preferably brought to a slightly alkaline pH to remove the carboxy proton and render the amino group electronegative and thus reacts with the metal stepwise as follows:

(1)
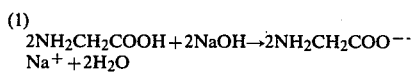

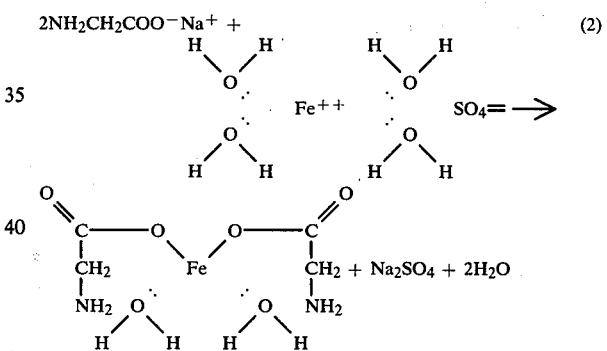

and then upon the addition of more base (NaOH) to a pH between about 7.5 and 10 the amino group is rendered more electronegative and the reaction is completed as follows:

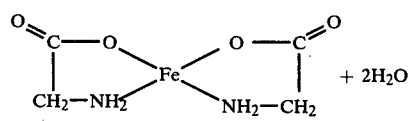

It will be seen that the ligands have replaced the waters of hydration and the base has reacted to remove the protons and form an alkali metal salt. This is for exemplification only and myriad reaction steps could be shown using various bases and ligands as well as different metals. It will be seen from the above why it is important that each proteinate consists of a metal and at least two ligands in order to completely neutralize any electrical charge.

The exact ligand used is not important, amino acids such as lycine, glycine, valine, methionine and the like may be used along with peptides and polypeptides.

While hydrolysates with a peptide bond are preferred as ligands, any example utilizing a protein hydrolysate ranging from naturally occurring amino acids to polypeptides is deemed to exemplify the invention in its best mode.

The same is true with metals. While iron, zinc, and copper may constitute the more important metals calcium, manganese, cobalt, molybdenum, and magnesium, may be equally as exemplary.

Plant hormones (phytohormones) are biologically active materials of plant origin that are effective in minute concentrations at sites remote from tissues in which they are formed. Cytokinins, auxins, gibberellin(s), abscisic acid and ethylene are the major classifications of phytohormones.

Kinetin was the first of the active cytokinins (having growth promoting properties) identified and is a 6-furfurylaminopurine having the formula:

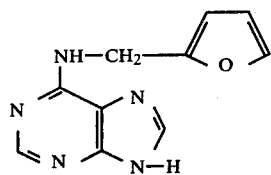

Other naturally occurring cytokinins involve:
dimethlallyl amino purine

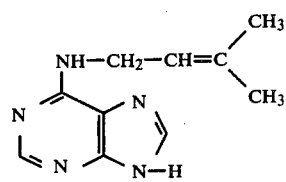

methylamino purine

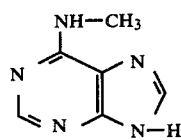

zeatin (methylhydroxymethylallylaminopurine)

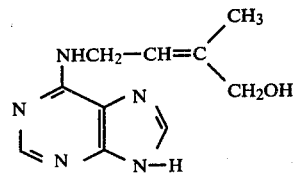

Zeatin has been isolated and chemically identified from young kernals of maize, coconut milk, plums, fungus, bacterium, lupin plants and other plants having soluble ribonucleic acid.

One may also find attached to the amino group phenyl, benzyl, n-ethyl, n-propyl, n-butyl and similar groups.

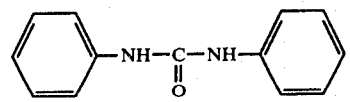

Diphenylurea, a synthetic compound, shown above also exhibits cytokinin activity.

Various cytokinins are found in different sources. Dimethylallylaminopurine occurs in soluble ribonucleic acid of many different organisms and is produced by bacterium corynebacterium fasians.

The bacterium and mutations from dimethylallylaminopurine invade green plants such as algae, chlorella, kelp and by secreting the compound produces cytokinin effects.

The dihydro-derivative of zeatin has been isolated from lupin plants and cytokinins have been isolated from the sporophyte of mosses.

The richest natural sources for kinins that have been isolated are seaweed, fruits, and endosperm tissues.

Diphenylura in the presence of casein hydrolysate is distinctively active in cytokinin effects.

Metals and plant hormones are inseparably connected. Dimethylallylaminopurine has been identified with the transfer of ribonucleic acid which combines with serine and tyrosine before these amino acids are incorporated into protein. This explains the cytokinin effect on ribonucleic acid, protein and chlorophyll levels, and indirectly plant growth. Zinc, manganese and iron are all involved in the process of plant growth. Magnesium is of course essential to chlorophyll formation.

Manganese activates the enzyme indoleacetic acid oxidase which controls the distribution of the growth regulators produced from auxins. This enzyme limits the amount of auxin in any area and prevents excessive amounts. It also deactivates auxin in nongrowing areas.

Zinc builds up the auxin hormone just as manganese regulates and controls the supply.

Iron activates an enzyme transport system that controls directions and movement of plant regulators.

Other minerals mentioned such as copper, boron, molybdenum, and magnesium also have important functions in plants.

Auxins greatly magnify the cytokinin effect. Added cytokinins increase mitosis in roots and encourage mitosis in cultural flower anthers.

Cytokinins are strong promoters of bud growth and leaf growth stimulation. Some other effects of cytokinins in plants result in ending dormancy, promote polarity of growth, promote flowering, increase effectiveness of light in said germination, and promote stem elongation.

The growth of a plant is regulated in an orderly way through photosynthesis and respiration. This is accomplished by sun, water, micronutrients such as molybdenum, manganese, zinc, iron and boron and enzymes and by growth hormones such as the naturally occurring auxin. Chemically speaking this auxin is indoleacetic acid. To be produced a mineral such as zinc is required to stimulate the plant enzyme system to refine the amino acid tryptophane into auxin.

Another mineral, manganese, is required to activate the enzyme indoleacetic acid oxidase which controls the distribution of the growth regulation produced by auxin or indoleacetic acid. As mentioned, manganese also aids in regulation of auxin in non-growing regions of the plant.

Auxins, cytokinins, and gibberellin(s) interact in plant growth development and cell division but oppose each other in lateral bud outgrowths.

There are many synthetic chemicals that behave like the naturally occurring auxins produced by plant enzyme systems. In addition to indoleacetic acids, indol-3-butyric acid; naphthaleneacetamide; 2 methyl-1-naphthaleneacetic acid and 2-methyl-1-naphthylacetamide have hormonal activity and may be substituted for the naturally occurring auxins. The synthetic auxins cannot function without zinc, manganese, and other minerals in the same requirement pattern as found with naturally occurring auxins. For best results, the minerals must be in the form of proteinates. As stated earlier the proteinate preferably has a peptide (—CONH—) bond.

One of the important aspects of plant growth and nutrition is nitrogen fixation. Nitrogen can enter biological systems only when it has been combined with other elements such as hydrogen and oxygen. Industrially nitrogen is converted into such compounds as ammonia, nitrate salts, urea or ammonium sulfate. Nature provides a way for nitrogen fixation using the molecular nitrogen gas ($N_2$) from the air and enzymatically combining it with hydrogen from carbohydrates or natural gas to form ammonia utilizing a nitrogenase. Certain bacteria also act to form ammonia. No substances between nitrogen and ammonia have been isolated, so all the intermediate states must be bound to the nitrogenase.

In the soil fixed nitrogen is employed in the synthesis of biological molecules. A critical structural element is the peptide bond (—CONH—) which links one amino acid to the next; the bond connects a nitrogen atom in one amino acid to a carbon atom in another. Several amino acids may be linked together to form a peptide or polypeptide which will ultimately form a protein.

A metal proteinate not only provides the plant with an essential trace metal but also has a nitrogen fixation sparing effect thus avoiding several steps in nitrogen fixation and allows the plant to absorb ligands containing the peptide bonds directly. This may be accomplished by means of soil application or foliar spray.

Phytohormones may be prepared synthetically or naturally. Cytokinins are primarily available as seaweed extracts. These extracts are diluted with water and used as foliar sprays or applied to the soil.

Kinetin may be prepared synthetically and has essentially the same activity as cytokinin. Gibberellin(s) have also been obtained from seaweed extracts but store less well than cytokinins or kinetin. Auxins have also been prepared from seaweed extracts.

Several beneficial aspects have been attributed to phytohormones including increased crop yields, improved seed germination, increased resistance of plants to frost, fungal and insect attack, increased uptake of inorganic constituents from the soil, reduction in storage losses of fruit and stabilization of chlorophyll. See Blunden, *Marine Natural Products Chemistry*, Plenum Publishing Corporation, N.Y., N.Y., 1001, pp 337-344.

Phytohormones are known carriers of certain inorganic substances into a plant but the amount of minerals is only a minute fraction of the total mineral requirement for the plant.

According to Brain et al, *The Effects of Aqueous Seaweed Extract on Sugar Beet,* Proceedings of the Eighth International Seaweed Symposium, University of North Wales, 1974, seaweed extracts are characterized by their high cytokinetic activity. The most important effects of cytokinins are on cell division, cell enlargement, the delaying of senescense and the related transport of nutrients.

One important factor is that cytokinins are very restricted in their movement within the plant, if indeed they move at all from the original site of application. Treated foliar areas act as metabolic sinks and amino acids, phosphates and other substances accumulate in the plant tissues directly under on close to the site of application. For optimal results the cytokinin or other phytohormones should apread throughout the plant. More is involved with phytohormones than the mere mobilization of nutrients, since the delay of senescence of excised plant parts has been demonstrated many times.

The observation that cytokinin treatment augmented the ratio of RNA to DNA, suggested that a critical effect of cytokinins in senescence might be the maintainence of the protein synthesizing machinery, perhaps by regulating RNA synthesis.

Insofar as sugar beets are concerned the translocation or spreading of cytokinin will increase the leaf size, protein content, chlorophyll and leaf life. Hence, the photosynthetic power of the plant would be increased with cytokinin translocation which would result in increased carbohydrate synthesis and increase the stored carbohydrate content of the root.

Aqueous seaweed extracts have successfully been used as fertilizer additives on bananas, gladiolas, tomatoes, peppers, potatoes, corn and oranges with varying degrees of success. Of special interest was the increased uptake of manganese in banana plants. Also of interest was the improved storage of peaches.

Logically, it is necessary to know the activity of the phytohormone being used so concentration can be regulated and optimal reproducable results obtained.

The class of phytohormones referred to as auxins may be natural or synthetic such as indoleacetic acid or 2.4-dichlorophenoxy acetic acid (b 2.4D.). These hormones are transported within the root from its base to its apex. Natural occurring auxins are not as stable in ambient air as synthetic auxins. Auxins in general move more rapidly to the root tip when applied to cotyledon or leaves. The movement presumably is accompanied with the transport of carbohydrates via the phloem. Since auxins, as contrasted to cytokinins, move more rapidly through the plant they are adapted to the treatment of seeds prior to planting. The consistent application of phytohormones helps reduce the usage of N.P.K. fertilizers by as much as 25%. Optimally, cytokinins, auxins, and gibberellin(s) are applied at a rate of 0.001 to 4.0 grams per acre. Preferably these phytohormones are utilized as dilute solutions containing on the order of 10–200 ppm of active ingredient and, if used in an alkaline media, are stabilized by a preservative such as sodium benzoate.

The root of a plant contains portions of the best known phytohormones and serve as a center for synthesis. The xylem and phloem being the major circulatory portions of a plant also serve as hormone carriers for those hormones that can be translocated. It has been documented that there are manifold effects of root hormones, expecially cytokinins, on shoot development. These include control of protein and $CO_2$ metabolism in leaves, enzyme formation in leaves, leaf aging and senescence, elongation of the shoot, stem elongation, lateral shoot development and release of floral bud dormancy, and fruit set.

Environmental influences which affect the root system such as water stress, flooding, excessive heat or cold act not only on water and ion uptake and transport of organic substrates but also on the hormonal flow from root to shoot and vice versa.

From the above discussion of phytohormones it may be seen that there is a complex interaction between nitrogen fixation and uptake, mineral uptake, phytohormone activity and their role in the translocation of ions and nutrients.

In recognizing the importance of a plant as a whole it becomes apparent that manipulation of the entire plant, including shoots, leaves, and roots by phytohormones and metal proteinates with selective field testing offers an almost limitless avenue in plant growth regulation and improvement.

DESCRIPTION OF THE INVENTION

It has now been found that there is a synergistic effect when phytohormones and metal proteinates are applied together. The sparing effect on nitrogen fixation is improved by the combined action of phytohormones and metal proteinates having one or more peptide bonds. When metal proteinates and phytohormones are applied as a foliar spray there is a nitrogen sparing effect on the enzyme function and ATP (adenosine tri-phosphate). The metal proteinates improve the translocation of phytohormones through the plant and supply the necessary nitrogen building blocks in the form of polypeptides, peptides and naturally occuring amino acids. Moreover once the chelate or metal proteinate bonds are broken, essential metal ions are made available to the plant to promote growth and maturity.

The nitrogen sparing effects of a synergistic mixture of metal proteinates and phytophormones greatly accelerates plant growth with less energy requirements. In nature a plant must either absorb nitrogen from the air and enzymatically convert the nitrogen to ammonia or soil bacteria surrounding root nodules must convert soil nitrogen into ammonia for plant absorption. The plant must then convert the ammonia into amino acids which then combine to form peptides, polypeptides and eventually proteins. This is an oversimplification of the nitrogen fixation process in nature. For example from 14 to 16 molecules of ATP (adenosine tri-phosphate) are required in photosynthesis to convert one molecule of ammonia into the simplist amino acid, glycine. The combination of metal proteinates plus phytohormones substantially short stops this complex process. The metal proteinates, assisted by the phytohormones, are absorbed directly by the plant through either the roots or leaves and nitrogen is immediately made available as a building block in the form of amino acids, peptides, or polypeptides, once the metal ligand bonds are broken. Thus the complex steps of converting nitrogen from the air into ammonia or of applying a commercial fertilizer such as ammonia, urea, or ammonium salts is substantially reduced or eliminated. The further steps of converting ammonia into amino acids followed by the formation of peptide bonds is also substantially reduced. The sparing effects on nitrogen fixation can thus be readily seen.

While metal proteinates or phytohormones used separately promote nitrogen sparing the additive effects of the combination is truly synergistic.

When metal proteinates along with one or more phytohormones such as auxins, cytokinins, and giberellin(s) are simultaneously added to plants, there is also noted a synergistic effect in other growth and regulatory effects of the plants such as fruiting, cell division, expansion of young leaves, formation of new shoots or root tissue, increased outgrowth of lateral buds, increased seed germination, mobilization of various metabolites to the point of phytohormone application and increased mitosis in roots.

Plant life and growth also depends on active enzymes to ensure a constant flow of growth substances, photosynthesis, respiration, protein formation, vitamins and hormone development. The interaction of minerals and enzymes are shown in the following table.

TABLE 1

| Enzyme | Mineral Activator |
| --- | --- |
| nitrate reductase | molybdenum |
| glutamic dehydrogenase | copper |
| phospholipase | manganese |
| cytochromase | iron |
| starch phosphorylase | boron |
| auxin enzyme | zinc |

The following table, Table 2, show the average trace mineral content in soils required for growing crops. All the data is measured in terms of parts of mineral per million parts of soil (PPM).

TABLE 2

| | Range in PPM | | |
| --- | --- | --- | --- |
| Mineral | Low | Adequate | High |
| Zinc | 10 | 20 | 100 |
| Manganese | 20 | 50–100 | 500 |
| Iron | 20 | 30–200 | 300 |
| Copper | 2 | 10–30 | 50 |
| Boron | 5 | 20 | 90 |

Some soils may require more or less as determined by soil analysis, pH of soil and other nutrients in the soil.

The average amounts of plant hormones to use to attain the desired biological effect are shown in Table 3. The hormone is measured in terms of parts per million as was the metal. Amounts may vary from 10–200 PPM but the average is given as follows:

TABLE 3

| | Concentration | |
| --- | --- | --- |
| Hormone | Low | High |
| Cytokinins | 50 | 100 |
| Auxins | 60 | 120 |
| Gibberellin(s) | 45 | 150 |

A typical formulation is listed in Table 4 showing the amount of minerals and hormones that can be mixed together. The minerals are present in the form of metal proteinates. The specific protein hydrolysate used is not important. What is essential is that there are at least two moles of protein hydrolysate per mole of mineral. The amount recorded is the amount of mineral present as a proteinate excepting boron which is applied as an inorganic salt.

TABLE 4

Dissolve in 10 gallons of water

| Mineral and phytohormone | Amount |
| --- | --- |
| Calcium | 2.0 lbs |
| Zinc | 0.5 lbs |

TABLE 4-continued

Dissolve in 10 gallons of water

| Mineral and phytohormone | Amount |
|---|---|
| Iron | 0.5 lbs |
| Manganese | 0.5 lbs |
| Boron | 0.25 lbs |
| Molybdenum | 0.10 lbs |
| Copper | 0.05 lbs |
| Cytokinin (Zeatin) | 60 mgs |
| Auxin (Indoleacetic acid) | 60 mgs |
| Gibberellin(s) | 40 mgs |

If desired, magnesium and potassium could also be added.

The above formulation could be diluted to one hundred gallons with water and used as a foliar spray on ten acres of corn, wheat, alfalfa and the like.

The content or ratio of active ingredients in the synergistic mixture may vary over a wide range. The content of such phytohormones may vary from about $10^{-5}$ to 4.0 grams per acre with $.10^{-3}$ to 2.0 grams being preferred. The metal content will usually be higher depending upon the metal used. Amounts of calcium and magnesium will be much greater than copper and molybdenum. These amounts will range from about .014 to 2.0 lbs of metal per acre utilized as a metal proteinate. Since the weight of the ligands combining with the metal to form a proteinate may vary widely it is not possible to accurately state the metal proteinate to phytohormone ratio. Stated in grams the metal is added in an amount that may range from about 0.45 to 900 grams per acre and preferrably from about 2 to 90 grams per acre are utilized. The ratio of active ingredients in a synergistic mixture will then range from about $10^{-5}$ to 4.0 parts by weight for each phytohormone used and from about 0.45 to 900 parts by weight of each metal used in the form of a metal proteinate: Perferably from about $.10^{-3}$ to 2.0 parts by weight of each phytohormone will be mixed with from about 2 to 90 parts by weight of each metal in the form of a metal proteinate.

Variations in the formula could obviously be made as dictated by the soil and/or plant deficiencies.

EXAMPLE 1

The following experiment was carried out to demonstrate the novelty of the above described invention. As a basis for comparison 6 tomato plants about 10 inches tall containing 6 leaves each were divided into 2 groups of 3 plants each.

To group 1 was added 2.5 microcuries of $Fe^{59}$ chelated with L-leucine which was put on a leaf.

A second group containing the same amount of microcuries of iron was applied to another leaf of the second group as iron sulfate.

Four days later the total corrected scintillation counts per minute was detected via a Chicago Nuclear Counter.

The results were as follows:
Non-chelated leaves 48 counts per minute.
Chelated leaves 2512 counts per minute.

This experiment demonstrates the superior absorption of mineral amino acid chelates over the same mineral used in inorganic form.

EXAMAPLE II

To point out the novelty of the present invention six tomato plants about 10 inches tall and containing 6 leaves per plant were divided into three groups of 2 plants each.

Group 1 received 2.5 microcurocuries of $Zn^{65}$ as a zinc L-leucine chelate to one leaf of each plant.

Group 2 received 2.5 microcuries of zinc chloride to one leaf of each plant.

Group 3 received 2.5 microcuries of zinc chelated with L-leucine plus a plant hormone mix applied to each leaf.

The zinc L-leucine chelate of Group I was prepared by mixing a solution containing 10 microliters of $Zn^{65}Cl_2$ containing 2.5 microcuries of $Zn^{65}$ and $4.81 \times 10^{-2}$ mg of Zn or $7.4 \times 10^{-4}$ millimoles of $ZnCl_2$ ith a solution containing 1 gram per 100 ml of L-leucine. The amino acid solution contained 0.2 mg of L-leucine or $15.2 \times 10^{-4}$ millimoles. To the above solution was added a buffer of 20 microliters of sodium carbonate-sodium bicarbonate solution (pH 10) and the entire mixture was diluted with 50 microliters of distilled water. This solution was applied to a tomato leaf of each plant by wetting a small piece of filter paper with the solution and placing the filter paper to the leaf.

The zinc chloride solution of Group 2 was prepared using the same zinc concentration and volume of buffer and water.

The zinc L-leucine chelate was prepared the same as in Group 1 solution to form the Group 3 solution except, instead of using 50 microliters of water, 30 microliters of distilled water and 20 microliters of a plant hormone solution was used. The plant hormone solution was prepared by dissolving the equivalent of plant hormones as follows:

Auxin (indoleacetic acid)—0.01 mg/liter
Cytokinin (Zeatin)—0.01 mg/liter
Gibberellin(s)—0.000.1 mg/liter One milliliter of this solution was diluted to 100 mls with distilled water and 20 microliters were added to the buffered amino acid chelated zinc solution.

Groups 2 and 3 were applied to tomato leaves on each plant via filter paper as in Group 1.

After four days the total corrected scintillation counts per minute was detected as in Example 1. The results were as follows:

| | Group 1 | Group 2 | Group 3 |
|---|---|---|---|
| Leaf (not at spot of application) | 139 | 10 | 298 |
| Alternate Leaf below leaf of application | 1.5 | 2.0 | 1.5 |
| Main stem | 9 | 5 | 3.3 |

From the above data the superiority of absorption of amino acid chelates as compared to the corresponding inorganic metal salts is demonstrated. The additive or synergistic effect of the phytohormones on the absorption of the amino acid chelates as compared to the amino acid chelates alone is specifically confirmed.

EXAMPLE III

The following experiments were conducted to demonstrate the increased mineral absorption and growth in wheat utilizing a control of inorganic iron and zinc, an amino acid chelated iron and zinc and a synergistic mixture of amino acid chelated iron and zinc along with the phytohormone mixture of Example II. The zinc proteinate contained 10% weight zinc as an amino acid chelate and the iron proteinate contained 7.5% weight iron as an amino acid chelate.

| Run # | Amount mineral or mineral and hormone added | Results of mineral uptake mg/gm |
|---|---|---|
| 1 | (control) | .15 iron |
|   |   | 1.58 zinc |
| 2 | 10cc zinc | 1.65 zinc |
| 3 | 10cc zinc | 2.46 zinc |
|   | 10cc phytohormone mix |   |
| 4 | 10cc iron | .28 iron |
| 5 | 10cc iron |   |
|   | 10cc phytohormone mix | .83 iron |

In order to obtain the above results all samples were thoroughly washed with de-ionized distilled water six times, ashed, then liquified by standard chemical techniques and assayed via atomic absorption spectrophotometer.

The results clearly show the advantage of utilizing both the amino acid chelate (metal proteinate) and phytohormone mix in plant growth.

EXAMPLE IV

Seeds in the stated amounts were each planted in vermiculite and allowed to germinate using standard watering procedures. A foliar spray was applied to the germinated seedlings and the height of the plants was measured from the vermiculite base at the end of three weeks. The metals were added as 10% by weight metal amino acid chelate at the rate of 900 gms/acre and the phytohormone mix of Example II was added at the rate of $2 \times 10^{-4}$ gms/acre.

| Seeds | Control | Zinc Proteinate | Iron Proteinate | Zinc Proteinate & Phytohormone Mix | Iron Proteinate & Phytohormone Mix |
|---|---|---|---|---|---|
| Wheat 1 oz. | 7" | 8" | 10" | 12" | 11.75" |
| Peas 1 oz. | 5" | 6.5" | 6.75" | 9" | 8.5" |
| Beans 1 oz. | 4.75" | 5.5" | 6" | 8.75" | 7.25" |
| Corn 1 oz. | 8" | 9.75" | 9.12" | 12.8" | 11.75" |
| Tomatoes ¼ oz. | 7" | 7.25" | 8" | 9.75" | 9.5" |

The results again confirm the synergistic advantage of utilizing the combined amino acid chelates with the phytohormones.

EXAMPLE V

A stock solution of iron sulfate was prepared by dissolving 7.95 gms of $Fe^{59}SO_4 \cdot 7H_2O$ per liter of water and diluting 40 parts by volume of the iron solution with 160 parts by volume of water.

A plant hormone solution was prepared containing 60 parts by million each of a cytokinin (Zeatin), auxin (indoleacetic acid) and gibberellic acid.

Chelates were made from the iron stock solution. An iron proteinate was made by mixing together equal volumes of iron stock solution, hydrolyzed vegetable protein solution (1.0 m), potassium hydroxide solution (1.0 m) and water. An EDTA chelate was also prepared by mixing equal volumes or iron solution and water with a double volume of disodium EDTA at an EDTA concentration of one gram per liter.

The following solutions were prepared for application to the leaves of tomato plants. Volumes are measured in terms of microliters and were applied as foliar sprays.

| A (Fe Proteinate) | B (EDTA Chelate) | C (Control) |
|---|---|---|
| 10 μl Stock | 10μl Stock | 10 μl Stock |
| 10 μl HVP | 20 μl EDTA-2Na | 20 μl $H_2O$ |
| 10 μl KOH | 10 μl $H_2O$ | 10 μl $H_2O$ |
| D (A + plant hormone) | E (B + plant hormone) | F (C + plant hormone) |
| 10 μl Stock | 10 μl Stock | 10 μl Stock |
| 10 μl HVP | 20 μl EDTA-2Na | 20 μl $H_2O$ |
| 10 μl KOH | 10 μl hormone | 10 μl hormone |
| 10 μl hormone |   |   |

Twenty-four hours after application, the plants were dried and counted on a radioactive counter for iron activity. Counts are reported in terms of cc/min/mg.

|   | A | B | C | D | E | F |
|---|---|---|---|---|---|---|
| Same leaf | 43.09 | 26.65 | 29.42 | 37.58 | 23.93 | 21.08 |
| Adjacent leaf | .15 | .11 | .20 | .37 | .13 | .14 |
| Same stem | .34 | .05 | .12 | .07 | .04 | .14 |

Solution D consisting of the plant hormone plus iron proteinate showed over double the activity of iron translocated to the adjacent leaf over solution A (iron proteinate) alone. A comparison of solutions B and E (EDTA chelate) alone and with plant hormone showed no synergism and solution F containing the inorganic iron sulfate salt plus plant hormone actually showed inferior translocation as compared to the use of iron sulfate alone. Each test was replicated three times and the above data is the average of all tests.

Although the examples and description as given form the preferred embodiments of the invention, it is recognized that they are exemplary only and that departures may be made therefrom without departing from the scope of this invention which is not limited to the specific details disclosed, but is to be accorded the full scope of the claims so as to include any and all equivalent combinations and processes.

I claim:

1. A composition for plant application consisting essentially of (1) an effective amount of an essential bivalent metal selected from the group consisting of zinc, iron, magnesium, manganese, copper, molybdenum, calcium, and cobalt and mixtures thereof wherein each metal present is in the form of a metal proteinate and (2) an effective amount of a plant hormone selected from the group consisting of cytokinins, auxins and gibberellins and mixtures thereof wherein the weight ratio of each metal present to each plant hormone present may vary from 0.1125 to $9 \times 10^7$ in an aqueous carrier.

2. A composition according to claim 1 wherein the weight ratio of each metal present to each plant hormone present may vary from 1 to $9 \times 10^4$.

3. A composition according to claim 1 wherein each metal proteinate contains a peptide bond.

4. A composition according to claim 3 wherein the plant hormone contains a cytokinin.

5. A composition according to claim 4 wherein the cytokinin is a member selected from the group consisting of 6-furfurylaminopurine, dimethylallylaminopurine, methylaminopurine, methylhydroxymethylallylaminopurine, phenylpurine, benzylpurine, n-ethylpurine, n-propylpurine and diphenylurea.

6. A composition according to claim 3 wherein the plant hormone contains an auxin.

7. A composition according to claim 6 wherein the auxin is a member selected from the group consisting of indoleacetic acid, indole-3-butyric acid, naphthaleneacetamide, 2 methyl-1-naphthaleneacetic acid, and 2-methyl-1-naphthaleneacetic acid, and 2-methyl-1-naphthaleneacetamide.

8. A composition according to claim 3 wherein the plant hormone contains gibberellin.

9. A method of nitrogen fixation sparing which comprises adding to a plant a composition consisting essentially of (1) an effective amount of an essential bivalent metal selected from the group consisting of zinc, iron, magnesium, manganese, copper, molybdenum, calcium and cobalt and mixtures thereof wherein each metal present is in the form of a metal proteinate and (2) an effective amount of a plant hormone selected from the group consisting of cytokinins, auxins and gibberellins and mixtures thereof wherein the weight ratio of each metal present to each plant hormone present may vary from 0.1125 to $9 \times 10^7$ in an aqueous carrier.

10. A method of increasing the translocation of essential bivalent metals plant which comprises adding to the plant a composition consisting essentially of (1) an effective amount of an essential bivalent metal selected from the group consisting of zinc, iron, magnesium, manganese, copper, molybdenum, calcium and cobalt and mixtures thereof wherein each metal present is in the form of a metal proteinate and (2) an effective amount of a plant hormone selected from the group consisting of cytokinins, auxins and gibberellins and mixtures thereof wherein the weight ratio of each metal present to each plant hormone present may vary from 0.1125 to $9 \times 10^7$ in an aqueous carrier.

11. A method of promoting plant growth which comprises adding to the plant a composition consisting essentially of (1) an effective amount of an essential bivalent metal selected from the group consisting of zinc, iron, magnesium, manganese, copper, molybdenum, calcium, and cobalt and mixtures thereof wherein each metal present is in the form of a metal proteinate and (2) an effective amount of a plant hormone selected from the group consisting of cytokinins, auxins and gibberellins and mixtures thereof wherein the weight ratio of each metal present to each plant hormone present may vary from 0.1125 to $9 \times 10^7$ in an aqueous carrier.

* * * * *